US012589259B2

(12) United States Patent
Ranganathan et al.

(10) Patent No.: US 12,589,259 B2
(45) Date of Patent: Mar. 31, 2026

(54) METHOD TO OPTIMALLY SPLITTING ARCS IN MODULATED ARC THERAPY (MAT) PLANS

(71) Applicant: Elekta, Inc., Atlanta, GA (US)

(72) Inventors: Vaitheeswaran Ranganathan, Bangalore (IN); Natarajan Ramar, Bangalore (IN); Bojarajan Perumal, Bangalore (IN)

(73) Assignee: Elekta, Inc., Atlanta, GA (US)

( * ) Notice: Subject to any disclaimer, the term of this patent is extended or adjusted under 35 U.S.C. 154(b) by 650 days.

(21) Appl. No.: 17/431,466

(22) PCT Filed: Feb. 21, 2020

(86) PCT No.: PCT/EP2020/054591
§ 371 (c)(1),
(2) Date: Aug. 17, 2021

(87) PCT Pub. No.: WO2020/169787
PCT Pub. Date: Aug. 27, 2020

(65) Prior Publication Data
US 2022/0118283 A1 Apr. 21, 2022

Related U.S. Application Data

(60) Provisional application No. 62/808,394, filed on Feb. 21, 2019.

(51) Int. Cl.
*A61N 5/10* (2006.01)
(52) U.S. Cl.
CPC ......... *A61N 5/1031* (2013.01); *A61N 5/1047* (2013.01)

(58) Field of Classification Search
CPC .. A61N 5/1031; A61N 5/1047; A61N 5/1081; A61N 5/103
See application file for complete search history.

(56) References Cited

U.S. PATENT DOCUMENTS

2014/0357931 A1 12/2014 Cheng
2018/0085596 A1* 3/2018 Peltola ................. A61N 5/1081

FOREIGN PATENT DOCUMENTS

WO 2011042819 A1 4/2011
WO 2017156419 A1 9/2017
WO 2018083072 A1 5/2018
WO 2020003026 A1 1/2020
WO 2020169787 8/2020

OTHER PUBLICATIONS

International Search Report and Written Opinion of PCT/EP2020/054591, dated Apr. 23, 2020.

(Continued)

*Primary Examiner* — Carolyn Fin
(74) *Attorney, Agent, or Firm* — Schwegman Lundberg Woessner, P.A.

(57) ABSTRACT

A non-transitory computer readable medium (26) stores instructions executable by at least one electronic processor (20) to perform a method (100, 200) of identifying possible arc segments for removal in a modulated arc therapy plan. The method includes: iteratively optimizing a modulated arc therapy plan for an initial arc segment; and computing a geometric freedom (GF) metric for each control point (CP) of the initial arc segment.

23 Claims, 6 Drawing Sheets

Beamlets in CP 1

Beamlets in CP 2

(56)　　　　　References Cited

OTHER PUBLICATIONS

Rana, Suresh et al "Feasibility of the partial-single arc technique in RapidArc planning for prostate cancer treatment." Chinese Journal of Cancer, vol. 32, No. 10 (2013) pp. 546-552.

Pursley, Jennifer et al "A Comparative Study of Standard Intensity-Modulated radiotherapy and RapidArc Planning Techniques for Ipsilateral and Bilateral head and Neck Irradiation", Medical Dosimetry, vol. 42, 2017, pp. 31-36.

Wala, Jeremiah et al "Optimal partial-arcs in VMAT treatment planning." Physics in Medicine & Biology, vol. 57, No. 18 (2012).

Tian, Zhen et al "Multi-GPU Implementation of a VMAT Treatment Plan Optimization Algorithm", Medical Physics, 2015.

Zwan, Benjamin J. et al "The Dosimetric Impact of Control Point Spacing for Sliding Gap MLC Fields", Journal of Applied Clinicla Medical Physics, vol. 17, No. 6, 2016.

Keshet, O. et al."Semi-Automatic Method to Select Partial Arcs for Segment Modulated Arc Therapy Planning", I.J. Radiation Oncology, Biology Physics, vol. 75, No. 3, 2009.

Rapidarc, Radiotherapy and Radiosurgery, Varian Medical Systems, 2012.

"International Application Serial No. PCT EP2020 054591, International Preliminary Report on Patentability mailed Sep. 2, 2021", 8 pgs.

* cited by examiner

100

Optimize arc segments — 102

Compute GF for CPs of arc segments — 104

Plot graph of GF metric vs. CP — 106

Determine GF values below a threshold — 108

Select groups of CPs with GF values below threshold as candidate arc segments — 110

METHOD TO OPTIMALLY SPLITTING ARCS IN MODULATED ARC THERAPY (MAT) PLANS

CROSS-REFERENCE TO PRIOR APPLICATIONS

This application is the U.S. National Phase application under 35 U.S.C. § 371 of International Application No. PCT/EP2020/054591, filed on Feb. 21, 2020, which claims the benefit of U.S. Provisional Patent Application Ser. No. 62/808,394, filed on Feb. 21, 2019. These applications are hereby incorporated by reference herein.

FIELD

The following relates generally to the medical therapy arts, MAT arts, MAT optimization arts, and related arts.

BACKGROUND

Modulated Arc Therapy (MAT), such as for example volumetric MAT (VMAT) or intensity MAT (IMAT), can be delivered as a partial-arc, a full single arc, or as multiple arcs. For complex cases where a large amount of beam modulation is required, delivery in a single arc requires significant slowing down of the gantry rotation and reduction of the dose rate to achieve dose distributions similar to intensity-modulated radiation therapy (IMRT). Instead, radiation may be delivered over multiple arcs, which provides the necessary degrees of freedom but will tend to increase the total treatment time and required number of monitor units. In addition, for many clinical cases, one might expect that appreciable beam modulation is only required over a critical angle range. In such cases, the gantry might move at maximal speed and with limited fluence over the angles where the radiation produces little or no beneficial effect. Additionally, because of the limit on the minimum dose rate, the beam cannot be entirely turned off over non-beneficial angles. Rotating the gantry through these angles increases the dose to critical structures, as well as increases the total number of monitor units (see, e.g., Rana, Suresh, and ChihYao Cheng. "Feasibility of the partial-single arc technique in RapidArc planning for prostate cancer treatment." *Chinese journal of cancer* 32, no. 10 (2013): 546; Dumane, V. A., J. Kao, S. Green, V. Gupta, and Y. Lo. "Comparison of full arcs, avoidance sectors, and partial arcs for RapidArc planning." *International Journal of Radiation Oncology* * *Biology* * *Physics* 78, no. 3 (2010): S820-S821; and Wala, Jeremiah, Ehsan Salari, Wei Chen, and David Craft. "Optimal partial-arcs in VMAT treatment planning." *Physics in Medicine & Biology* 57, no. 18 (2012): 5861). Eliminating this portion of the arc from the delivery can reduce the treatment time and total MU and also decrease the dose to healthy tissue.

Existing methods for automatically finding the optimal partial/split-arcs that eliminate the unneeded arc segments are disclosed in Wala et al.) Though this method eliminates avoidable arc segments from the arc, it is acknowledged that the method disclosed therein is highly time consuming as it applies a global search technique to detect avoidable arc-segments.

The following discloses certain improvements.

SUMMARY

In some embodiments disclosed herein, a non-transitory computer readable medium stores instructions executable by at least one electronic processor to perform a method of identifying possible arc segments for removal in a modulated arc therapy plan. The method includes: iteratively optimizing a modulated arc therapy plan for an initial arc segment; and computing a geometric freedom (GF) metric for each control point (CP) of the initial arc segment.

In some embodiments disclosed herein, a system for identifying possible arc segments for removal in a modulated arc therapy plan includes at least one electronic processor programmed to: iteratively optimize a modulated arc therapy plan for an initial arc segment; compute a GF metric for each CP of the initial arc segment; and determine contiguous groups of CPs with GF metric values below a pre-selected threshold as candidate arc segments for removal from the modulated arc therapy plan.

In some embodiments disclosed herein, a method of identifying possible arc segments for removal in a modulated arc therapy plan includes: iteratively optimizing a modulated arc therapy plan for an initial arc segment; computing a GF metric for each CP of the initial arc segment by operations including computing a ratio, for each beamlet of the CP, of a number of tumor voxels touched by a beamlet divided by a sum of a number of voxels of critical organs touched by the beamlet; and summing the GF values for the beamlets of the CP to generate the GF metric for the CP; determining contiguous groups of CPs with GF metric values below a pre-selected threshold as candidate arc segments for removal from the modulated arc therapy plan; and estimating a re-distribution of a dose of the modulated arc therapy plan with the candidate arc segments removed from the modulated arc therapy plan.

One advantage resides in eliminating avoidable arc segments in MAT.

Another advantage resides in eliminating avoidable arc segments in MAT to reduce treatment time.

Another advantage resides in providing a MAT plan without impacting a dosimetric quality of the plan.

Another advantage resides in determining an impact of avoiding a particular arc segment in a MAT plan.

Another advantage resides in determining where to split an arc segment in a MAT plan.

Another advantage resides in determining an arc segment length in a MAT plan.

Another advantage resides in determining a number of splits in an arc segment in a MAT plan.

Another advantage resides in determining a minimum arc segment length in a MAT plan to produce a clinical acceptable plan.

Another advantage resides in producing a MAT plan with reduced computational capabilities.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
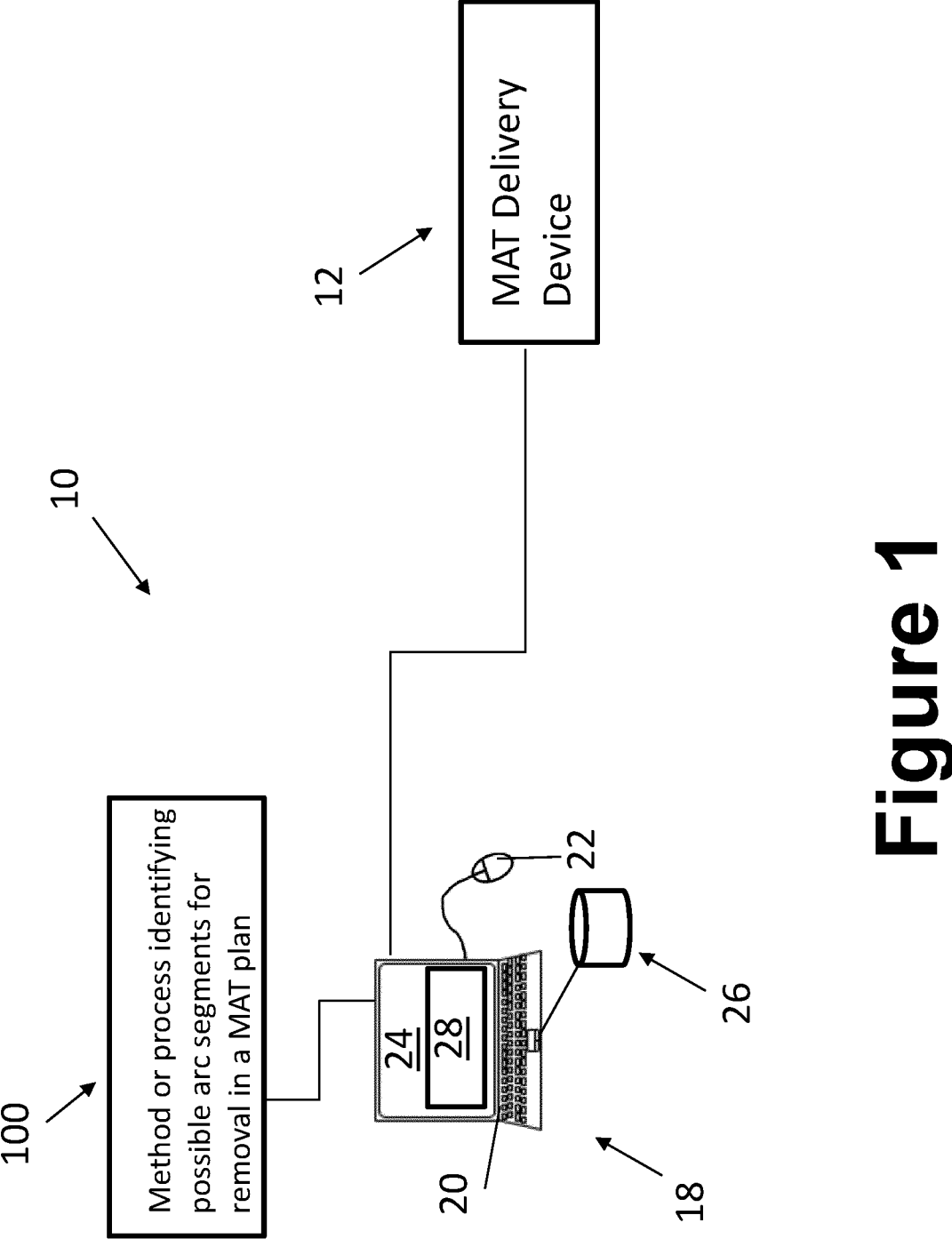
FIG. 1 diagrammatically illustrates a system for optimizing a MAT plan in accordance with one aspect.

In MAT radiation therapy, for example, VMAT, a full 360° circumferential arc is sometimes not necessary. For example, in the case of a small tumor there may be one or more arc segments over which interference from critical organ(s) limit the freedom to apply radiation to the tumor. In current clinical practice, the dosimetrist handles this in an ad hoc way, by identifying and removing arc segments that are expected to be of little therapeutic value based on the anatomical layout and then performing the VMAT optimization without those segments. Such an approach is subjective and does not provide a principled basis for removing segments.

The disclosed approach for identifying arc segments for removal from the VMAT plan operates as follows. First, the VMAT plan is optimized for the full arc (typically a full 360°, although a smaller "full arc" could serve as the starting point). A "geometric freedom" (GF) metric is computed for each control point (CP) of the arc. The disclosed GF metric for a beamlet is a ratio of the (optionally weighted) number of tumor voxels touched by the beamlet divided by a sum of the number of voxels of each critical organ touched by the beamlet (again optionally weighed for each critical organ). The GF for the CP is then the sum of the GF values for each beamlet making up the beam at that control point. The GF is plotted as a function of CP along the arc. A low value of the GF for a CP means the control point is "viewing" more critical organ tissue than tumor tissue, so that there is little freedom to use this CP to deliver significant radiation to the tumor. A contiguous group of CPs with low GF therefore presents a potential (i.e. candidate) arc segment for removal.

In addition to, or alternative to, plotting the disclosed GF versus CP along the arc, other relevant metrics could be plotted. These could leverage dose information available from the already generated VMAT plan for the full arc, e.g. the dose per CP could be plotted, or even more specifically the tumor dose and/or critical organ dose(s) per CP. Based on the plot(s), the user is provided with vertical cursors superimposed on the displayed graph, with which a candidate removal arc segment is selected.

After selection of a candidate removal arc segment, the impact of this removal is estimated as an estimated redistribution of the dose. The premise here is that the total dose to be delivered is likely to be a relatively fixed quantity, so that what needs to be estimated is a redistribution of the dose planned for delivery in the candidate arc segment to the remainder of the arc. The GF is recognized to be a good indicator as to how to re-distribute this dose, since a high GF for a CP means that the beam at the CP delivers most of its radiation to the tumor rather than to critical organ(s), whereas a low GF implies the opposite. The re-distribution of dose from the CP of the candidate removal arc segment to the remaining CPs is scaled by the GP of those CPs.

With the redistributed dose per CP estimated, the dose objectives and/or other metrics of VMAT plan quality can also be estimated for the re-distributed dose, and these can be displayed for consideration by the user. As the redistribution computation is done based on geometric factors (e.g. the GF) and the initial VMAT plan, it is computed without performing an iterative dose optimization and accordingly is fast. Hence, if the resulting redistributed dose is unacceptable the candidate removal arc segment can be adjusted (usually made smaller) and the redistributed dose recalculated; this can be repeated as needed to arrive at an acceptable removal arc segment (or to decide that no arc segment removal is appropriate). In some contemplated embodiments, the dose redistribution and plan metrics for the redistributed dose are computed in near real-time in response to the user adjusting the candidate removal arc segment via the vertical cursors. In this way, the user can quickly assess the likely impact of various possible removal arc segments, and choose a final removal arc segment.

Since the redistributed dose per CP estimated above is only an estimate, and moreover does not provide the detailed dose-per-beamlet for each CP, a single iterative dose optimization is performed at the end for the arc without the finally selected arc segment removed, and this final VMAT plan is reviewed/approved by the dosimetrist.

The initial selection of the candidate removal arc segment could be automated, for example by automatically selecting the largest contiguous group of CPs for which every GF is below a (possibly user-selectable) selection threshold. Adjustment of the removal arc segment could also be automated, e.g. if the dose objectives for the redistributed dose do not meet some acceptance criteria then the removal arc segment is reduced by some preset amount (or alternatively the CF selection threshold is reduced).

As used herein, the term "modulated arc therapy" (MAT) (and variants thereof) refers to any other suitable MAT therapy plan utilizing delivery of therapeutic radiation as the radiation source moves along an arc, rather than at a few fixed angles (e.g., VMAT, IMAT, and so forth). The following is described primarily in terms of VMAT.

As used herein, the term "arc segment" (and variants thereof) refers to a portion of MAT therapy including arc segments with a range of up to a 360°. In addition, a "full" arc segment is not necessarily a full 360° segment.

With reference to FIG. 1, a system 10 for optimizing a MAT plan is diagrammatically illustrated. The system 10 is associated with a MAT delivery device 12 for delivering MAT therapy to a patient according to a plan generated by the system. The system 10 includes a computing device 18 (e.g., a workstation, a computer, a tablet, a smartphone, and so forth). The workstation 18 comprises a computer or other electronic data processing device with typical components, such as at least one electronic processor 20, at least one user input device (e.g., a mouse, a keyboard, a trackball, and/or the like) 22, and a display device 24. It should be noted that these components can be variously distributed. For example, the electronic processor 20 may include a local processor of a workstation terminal and the processor of a server computer that is accessed by the workstation terminal. In some embodiments, the display device 24 can be a separate component from the computer 18. The workstation 18 can also include one or more databases or non-transitory storage media 26 which may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth. The display device 24 is configured to display a graphical user interface (GUI) 28 including one or more fields to receive a user input from the user input device 22.

The system 10 is configured to perform a method or process 100 of identifying possible arc segments for removal in a MAT plan. The non-transitory storage medium 26 stores instructions which are readable and executable by the at least one electronic processor 20 of the workstation 18 and to perform disclosed operations including performing the method or process 100. In some examples, the method 100 may be performed at least in part by cloud processing.

Figure 2:
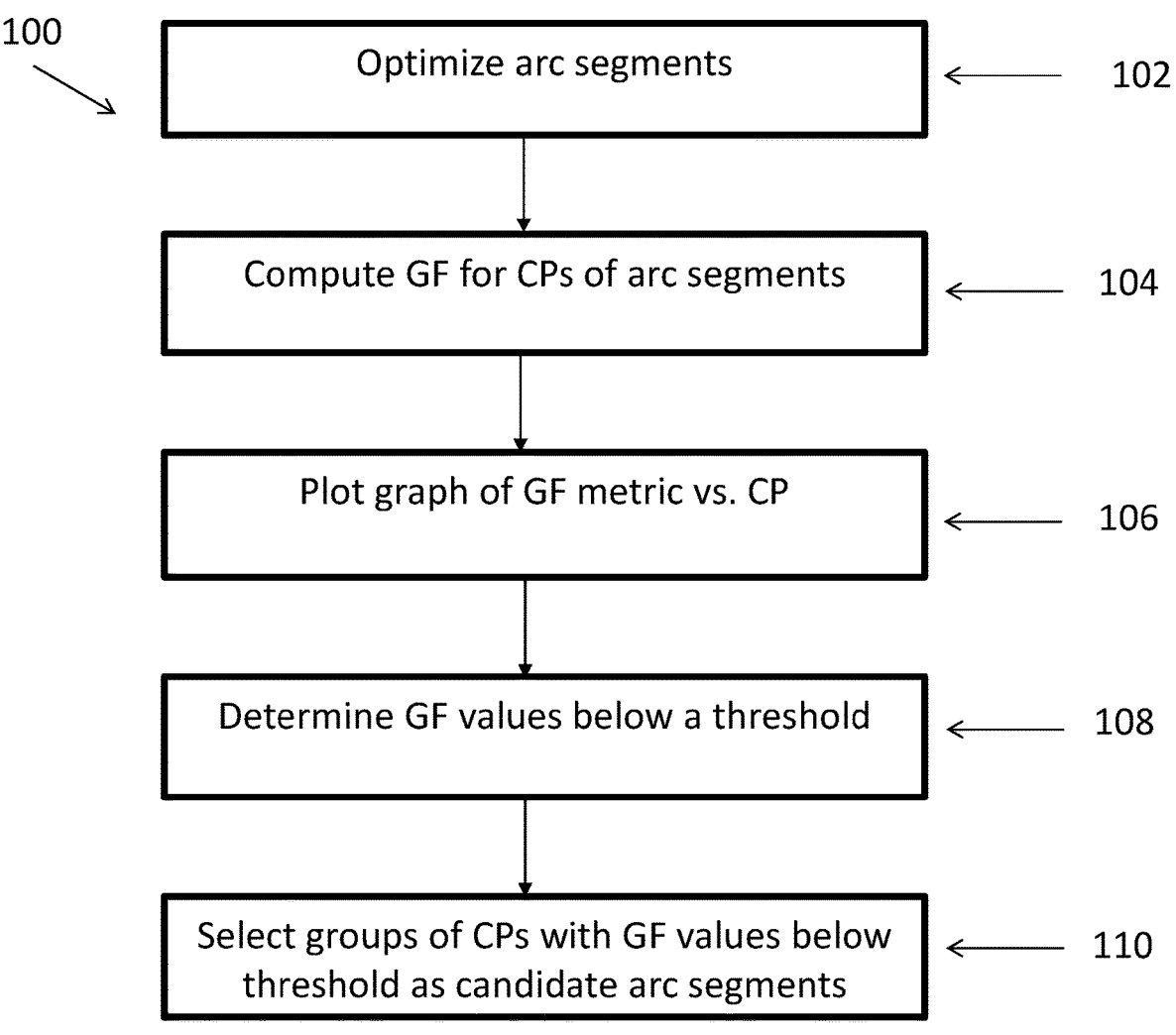
FIG. 2 shows an exemplary flow chart operation of the system of FIG. 1.

With reference now to FIG. 2, an illustrative method of identifying possible arc segments for removal in a MAT plan suitably performed by the system 10 of FIG. 1 (e.g., executable by the at least one electronic processor 20) is described. At 102, a MAT plan is iteratively optimized for an initial (i.e., first) arc segment. For example, the MAT plan is optimized by performing a single iterative dose optimization for the arc without any arc segments selected for removal. Thus, a "baseline" MAT plan including each arc segment is used as template to determine candidate arc segments for removal.

At 104, a geometric freedom (GF) metric is computed for each control point (CP) of each arc segment. The computed GF metrics can be stored, for example, in the non-transitory computer readable medium 26. In some embodiments, the GF metric is computed for each CP of the initial arc segment based on geometrical contours of the patient and a position of the CP, but not based on the modulated arc therapy plan. The geometric contours are contours of a tumor and one or more critical organs (e.g., liver, heart, lungs, and so forth). In other embodiments, the GF metric is computed by computing a ratio, for each beamlet of the CP, of a number of tumor voxels (e.g., voxels bordering the tumor) touched by a beamlet divided by a sum of a number of voxels of critical organs touched by the beamlet. The GF values for the beamlets of the CP are summed to generate the GF metric for the CP. In this example, the computing of the ratio can include weighting at least one of (i) the number of tumor voxels touched by the beamlet, and (ii) a number of voxels of critical organs touched by the beamlet.

At 106, a graph of the GF metric as a function of each CP along the initial arc segment is plotted on the display device 24. In addition, a tumor dose per CP and/or a critical organ dose per CP from the MAT plan can also be plotted on the display device 24. From the displayed plot(s), a radiologist can select candidate arc segments for removal from the MAT plan.

In some embodiments, the selection of candidate arc segments can be performed by the at least one electronic processor 20. At 108, GF metric values are determined as a function of CP on the graph being below a preselected threshold. At 110, contiguous groups of CPs with GF metric values below the pre-selected threshold are determined as candidate arc segments for removal from the MAT plan.

In one example, to determine the candidate arc segments, a re-distribution of a dose of the modulated arc therapy plan is estimated with the candidate arc segments removed from the MAT plan. To do so, the re-distribution of the dose of the MAT plan delivered by the candidate arc segments is estimated relative to remaining arc segments. This estimation can be performed by scaling the candidate arc segments to the remaining arc segments by the GP metric of each of the remaining arc segments. The re-distribution of the dose of the MAT plan can be plotted on the display device 24.

In another example, dose objectives of the MAT plan are estimated with the GF metrics of each CP and an initial modulated arc therapy plan. The dose objectives can be re-estimated when below a preselected threshold by adjusting a size of at least one of the candidate arc segments until the dose objectives are no longer below the preselected threshold.

Once the selected arc segments are removed, an updated MAT plan is generated and used to delivery therapy to the patient. The updated MAT plan shows a radiologist several factors, including an impact of avoiding a particular arc segment on a quality of the MAT plan, an impact of avoiding a particular arc segment on treatment time, a position of where to split an arc segment, an arc segment length, a number of splits in an arc segment, a minimum length of an arc segment that can produce a clinically acceptable plan, and so forth. In particular, the plots displayed on the display device 24 can include the GF profiles of all CPs in the MAT plan, one or more potentially avoidable arc-segments, and/or a re-distributed dose distribution after eliminating potentially avoidable arc-segment(s).

EXAMPLE

Figure 3:
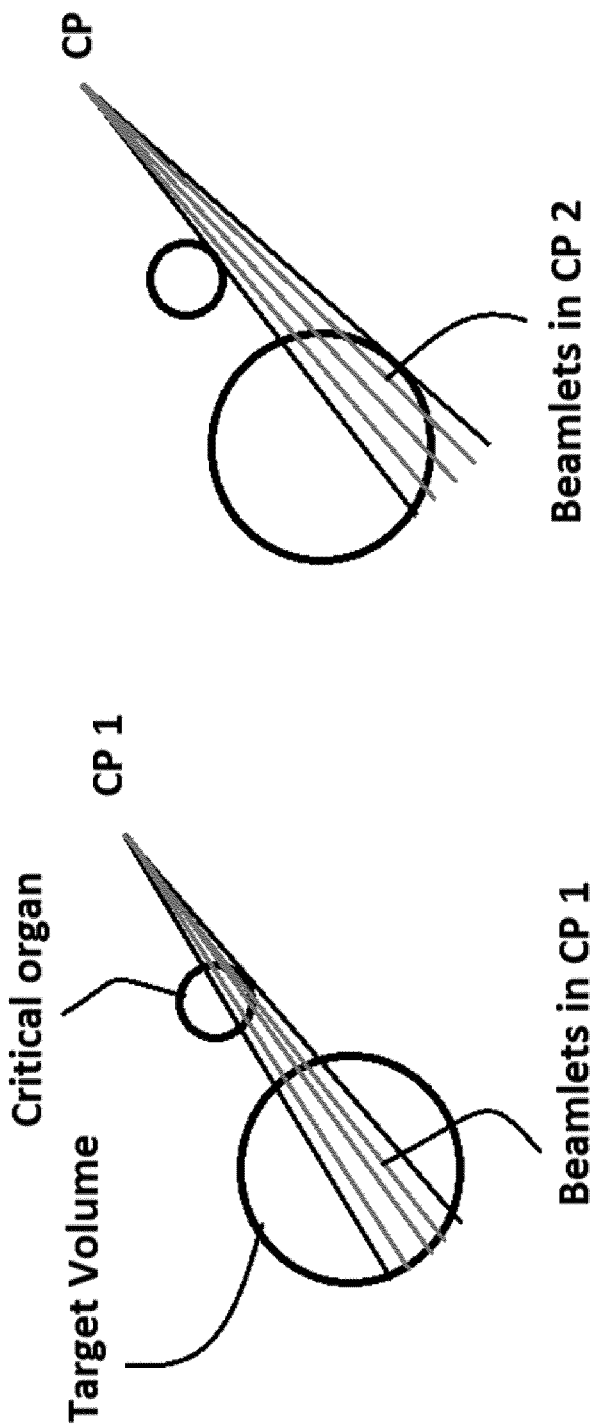
FIG. 3 shows an example of a computation of a GF metric of a CP of an arc segment of the MAT plan using the system of FIG. 1.

The following example describes in more detail how the candidate arc segments are selected. In a first step, a conventional "full" arc MAT plan is created. In a second step, the GF metric of each CP in the plan. The GF metric measures the relative freedom of a given CP to deposit the prescribed nominal dose to the corresponding target voxels. For instance, if a particular CP allows radiation to pass through the target voxels without passing through any critical organ voxels in the same path (i.e., before and after target volume), the GF of that CP is relatively higher. Likewise, if a particular CP allows radiation to pass through the same target voxels by passing through critical organ voxels (i.e., before and after target volume), the GF of the CP will be relatively lower. This concept is illustrated in FIG. 3.

Figure 4:
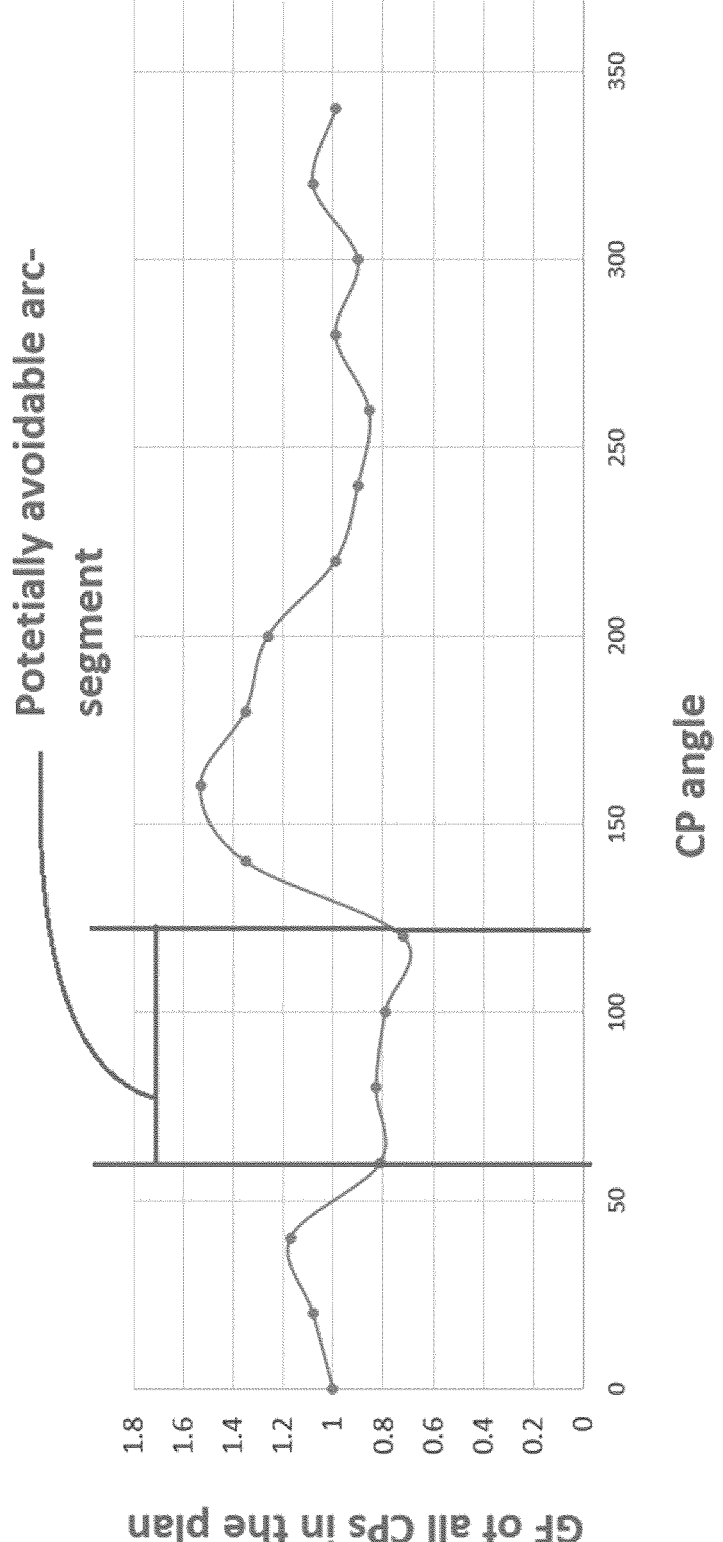
FIG. 4 shows a model plot to identify avoidable arc segments using the system of FIG. 1.

The actual computation of the GF metric for each CP involves profiling each beamlet in the CP and computing the GF metric for individual beamlets. The sum of the GF metrics of each individual beamlet in a CP are the GF of that CP. When computing the GF metric for a given beamlet in a given CP, clinical importance weighting factors can be applied for the target and critical organ voxels. Thus, the GF metric of a beamlet can be expressed by Equation 1:

$$GF_{beamlet\ of\ CP} = (W_t \times N_t) / \{1 + [(W_{c1} \times N_{c1}) + (W_{c2} \times N_{c2}) + \dots (W_{cn} \times N_{cn})]\} \quad (1)$$

where $W_t$ is the weightage assigned to target voxels, $N_t$ is the number of target voxels touched by the beamlet, $W_{c1}$ is the weightage assigned to critical organ 1, $N_{c1}$ is the number of critical organ 1 voxels passed through by the beamlet, and so on. The GF metric for a complete CP is determined as the sum of the GF metrics of the beamlets comprised by the CP. If GF profile of each CP is plotted in a graphical format on the display device 24, as shown in FIG. 4, a user can quickly identify the arc-segments that are potentially avoidable.

In a third step, in order to ensure that the identified arc-segment is indeed avoidable from the optimization point of view, the impact of eliminating the arc-segment needs to be objectively estimated. This can be done by performing a re-optimization of the MAT plan after creating a partial arc eliminating the identified arc-segment. But this is highly time-consuming and most importantly, if the quality of resulting plan is not acceptable, the user may get frustrated. Hence there should be a way to quickly and objectively assess the impact of removing an arc-segment without performing re-optimization.

7

Figure 5:
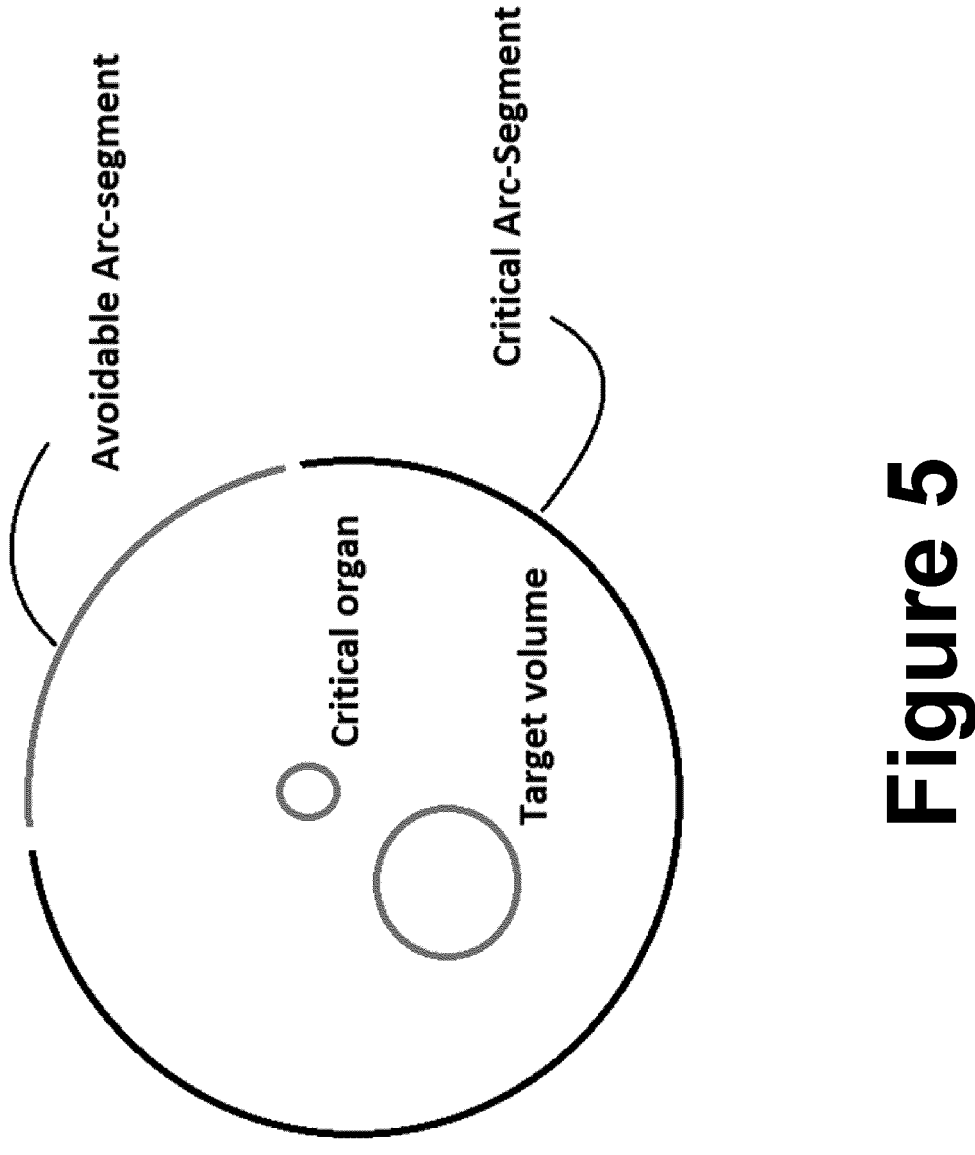
FIG. 5 shows an exemplary illustration of an avoidable arc segment and critical arc segment in a full MAT arc.

To remedy these problems, a GF guided dose redistribution (GFDR) process is performed. To do so, a dose contribution is removed from the identified potentially avoidable arc segment. The eliminated dose contribution can be redistributed among the CPs corresponding to the critical arc-segment (i.e. the rest of the arc after removing potentially avoidable arc-segment) scaled according to the GF value of each CP. This concept is illustrated in FIG. 5.

For instance, if amount of dose D is removed from target volume due to the elimination of an arc-segment, the dose amount D can be redistributed to the CPs of critical arc-segment based on their pre-computed GF values, which is expressed in Equation 2:

$$^{new}D_{cp}=D_{cp}+(D/N)\times^{norm}GF_{cp} \quad (2)$$

where $^{new}D_{cp}$ is a redistributed dose, D is the total dose to be redistributed among the CPs; $D_{cp}$ is the dose contribution of the CP to target before performing the proposed redistribution of dose; N is the total number of CPs in critical arc-segment and $^{norm}GF_{cp}$ is the normalized GF of the given CP.

Once the amount of dose contribution to be added to a given CP is found, a new monitor unit (MU) of the same CP can be determined according to Equation 3:

$$^{new}MU_{cp}=^{old}MU_{cp}+(^{cp}MU_0\times(D/N)\times^{norm}GF_{cp}) \quad (3)$$

where $^{new}MU_{cp}$ is the new MU of the CP in critical arc-segment, $^{old}MU_{cp}$ is the MU of the CP before performing redistribution of dose, $^{cp}MU_0$ is the MU per unit deposition of dose for the given CP.

In the dose redistribution scheme, the CP corresponding to the critical arc-segment with greater GF metric can get a larger share of additional dose contribution to target volume, while the CP corresponding to the critical arc-segment with lesser GF metric can get a relatively lower share of additional dose contribution to target volume. The dose redistribution scaled using the GF metric of each CP allows a near-optimal redistribution of the removed dose contribution from the tumor without performing actual optimization. Since this GFDR process does not involve any iterative processes and optimization, the user can instantaneously get to the see the dose distribution.

In a fourth step, the MAT plan with candidate arc segments removed can be objectively evaluated. if the redistributed dose after eliminating the avoidable-arc segment does not significantly increase the dose to critical organs, the user can opt for removing the potentially avoidable arc-segment from the MAT plan. Likewise, if the redistribution causes significant increase of dose to critical organs, the user can either reduce the length of the potentially avoidable arc-segment and either repeat the second and third steps, or go with a full arc. Though the proposed approach of geometry guided redistribution of dose may not match an actually reoptimized dose distribution in terms of ability to produce good dosimetric results, the user can make use of such intermediate and fast solutions for making critical decisions in shorter time. The user can be always aware that the results obtained after re-optimization can be almost always better than that obtained after dose redistribution. By considering for this factor, the user can evaluate the results obtained after dose redistribution. Considering this fact, optionally a correction factor can be provided to correct the results obtained after dose redistribution to improve the prediction accuracy.

An important advantage of the proposed approach is that it allows the user to approximately compute the impact of eliminating an avoidable arc-segment in total MU of the plan using the equations described in previous sections. This allows the user to guess if eliminating the arc-segment could really be of any use in reducing the treatment time or not. For instance, for peripherally located tumors, one can easily visualize that removal of an avoidable arc-segment from the farther side of tumor and redistributing the dose to critical arc-segment using the GF metric guided method can indeed result in reduced total MU.

Figure 6:
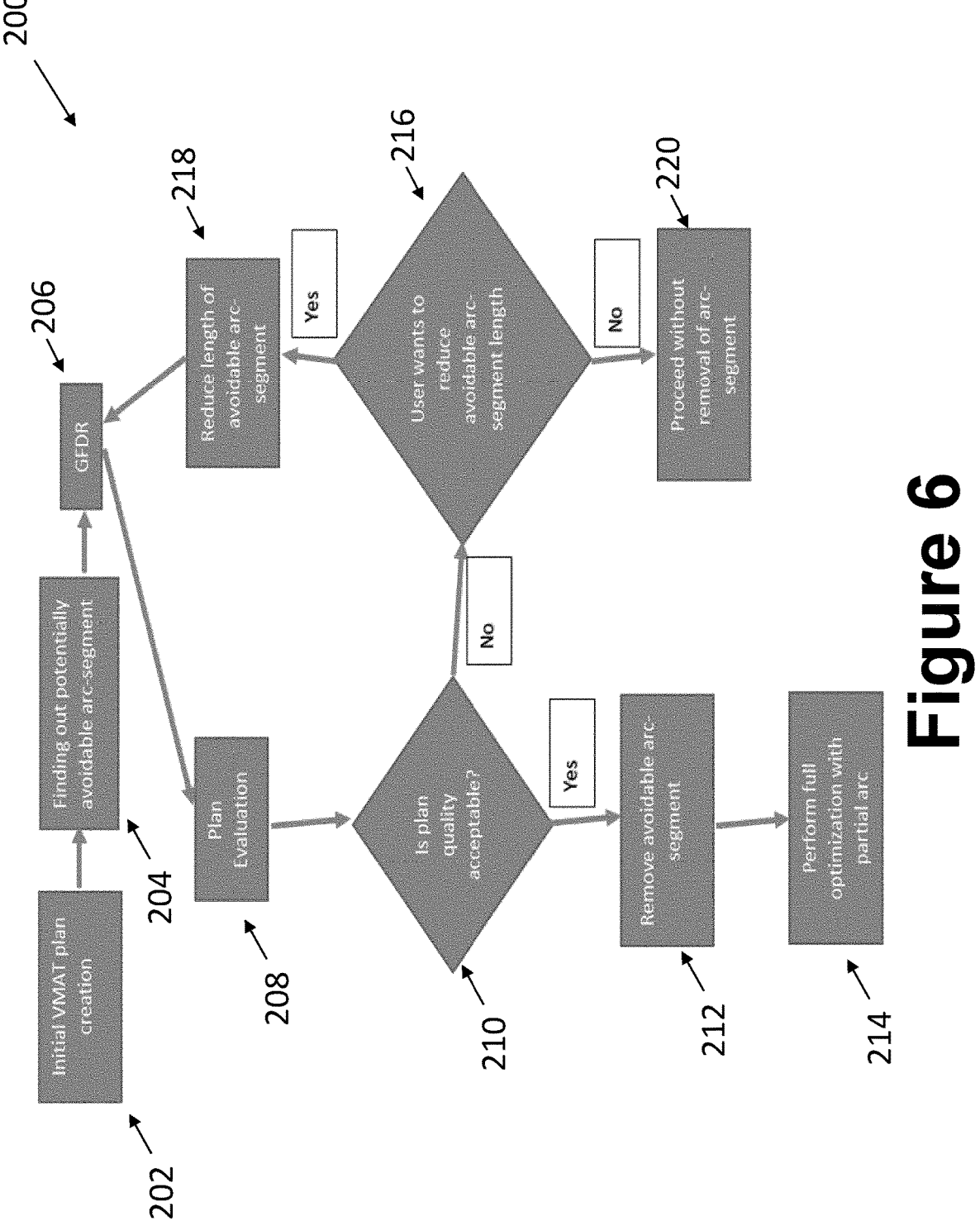
FIG. 6 shows another exemplary flow chart operation of the system of FIG. 1.

FIG. 6 shows another exemplary flow chart of a method or process 200 of identifying possible arc segments for removal in a MAT plan. At 202, an initial MAT (e.g., VMAT) plan is created. At 204, one or more potentially avoidable arc segments are found. At 206, the GFDR process is performed to determine a redistributed dose with the potentially avoidable arc segments removed. At 208, the new MAT plan with the redistributed dose is evaluated. At 210, the user determines whether the quality of the new plan is acceptable. If yes, then the avoidable arc segments are removed (at 212) and a full optimization is performed with a partial arc segment (at 214). If the user determines at 210, that the new plan is not acceptable, the user determines at 216 whether to reduce a length of the avoidable arc segment. If so, then at 218, the length of the arc segment is reduced at the GFDR process at 206 is repeated. If not, then at 220 the user proceeds without the removal of the arc segment.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium storing instructions executable by at least one electronic processor to perform a method of identifying possible arc segments for removal in a modulated arc therapy plan, the method comprising:

iteratively optimizing a modulated arc therapy plan for an initial arc segment; and computing respective geometric freedom (GF) metrics for each control point (CP) of the initial arc segment, wherein an individual GF metric indicates whether a specified nominal dose of radiation can pass through target voxels associated with a corresponding CP without passing through an identified critical organ voxel.

2. The non-transitory computer readable medium of claim 1, wherein the method further includes:

plotting, on a display device, a graph of the GF metric as a function of each CP along the initial arc segment.

3. The non-transitory computer readable medium of claim 1, wherein the GF metric is computed for each CP of the initial arc segment based on geometrical contours of a patient and a position of the CP but not based on the modulated arc therapy plan.

4. The non-transitory computer readable medium of claim 1, wherein computing a GF metric for each CP of the initial arc segment includes:

computing GF values, an individual GF value including a ratio, for each beam let of the CP, of a number of tumor voxels touched by a beamlet divided by a sum of a number of voxels of critical organs touched by the beamlet;

summing the GF values for the beamlets of the CP to generate the GF metric for the CP.

5. The non-transitory computer readable medium of claim 4, wherein the computing of the ratio further includes:

weighting at least one of (i) the number of tumor voxels touched by the beamlet, and (ii) a number of voxels of critical organs touched by the beamlet.

6. The non-transitory computer readable medium of claim 1, further including:

plotting, on a display device, at least one of a tumor dose per CP and a critical organ dose per CP from the modulated arc therapy plan.

7. The non-transitory computer readable medium of claim 1, further including:

determining GF metric values as a function of CP on a graph being below a preselected threshold; and determining contiguous groups of CPs with GF metric values below the preselected threshold as candidate arc segments for removal from the modulated arc therapy plan.

8. The non-transitory computer readable medium of claim 7, wherein determining contiguous groups of CPs with GF metric values below the preselected threshold as candidate arc segments for removal from the modulated arc therapy plan further includes:

estimating a re-distribution of a dose of the modulated arc therapy plan with the candidate arc segments removed from the modulated arc therapy plan.

9. The non-transitory computer readable medium of claim 8, further including:

estimating the re-distribution of the dose of the modulated arc therapy plan delivered by the candidate arc segments relative to remaining arc segments.

10. The non-transitory computer readable medium of claim 9, wherein the estimating includes:

scaling the candidate arc segments to the remaining arc segments by the GF metric values of each of the remaining arc segments.

11. The non-transitory computer readable medium of claim 8, further including:

plotting, on a display device, the re-distribution of the dose of the modulated arc therapy plan.

12. The non-transitory computer readable medium of claim 7, further including:

estimating dose objectives of the modulated arc therapy plan with the GF metrics of each CP and an initial modulated arc therapy plan; and re-estimating the dose objectives when below a preselected threshold by adjusting a size of at least one of the candidate arc segments until the dose objectives are no longer below the preselected threshold.

13. The non-transitory computer readable medium of claim 7, wherein the optimizing comprises:

performing an iterative dose optimization for the are without the candidate arc segments being removed.

14. A system for identifying possible are segments for removal in a modulated arc therapy plan, the system comprising:

at least one electronic processor programmed to:

iteratively optimize a modulated arc therapy plan for an initial arc segment;

compute respective geometric freedom (GF) metrics for each control point (CP) of the initial arc segment, wherein an individual GF metric indicates whether a specified nominal dose of radiation can pass through target voxels associated with a corresponding CP without passing through an identified critical organ voxel; and determine contiguous groups of CPs with GF metric values below a pre-selected threshold as candidate arc segments for removal from the modulated arc therapy plan.

15. The system of claim 14, further including a display device; and wherein the at least one electronic processor is programmed to:

plot, on the display device, a graph of the GF metric as a function of each CP along the initial arc segment;

determine GF metric values as a function of CP on the graph being below the pre-selected threshold; and determine contiguous groups of CPs with GF metric values below the pre-selected threshold as candidate arc segments for removal from the modulated arc therapy plan.

16. The system of claim 14, wherein the at least one electronic processor is programmed to determine the contiguous groups of CPs with GF metric values below the pre-selected threshold as candidate arc segments for removal from the modulated arc therapy plan by:

estimating a re-distribution of a dose of the modulated arc therapy plan with the candidate arc segments removed from the modulated arc therapy plan.

17. The system of claim 16, wherein the at least one electronic processor is programmed to:

estimate the re-distribution of the dose of the modulated arc therapy plan delivered by the candidate arc segments relative to remaining are segments.

18. The system of claim 17, wherein the at least one electronic processor is programmed to:

scale the candidate arc segments to the remaining arc segments by the GF metric values of each of the remaining arc segments.

19. The system of claim 18, wherein the at least one electronic processor is programmed to:

plot, on a display device, the re-distribution of the dose of the modulated arc therapy plan.

20. The system of claim 14, wherein the at least one electronic processor is programmed to:

estimate dose objectives of the modulated arc therapy plan with the GF metrics of each CP and an initial modulated arc therapy plan; and re-estimate the dose objectives when below a preselected threshold by adjusting a size of at least one of the candidate arc segments until the dose objectives are no longer below the preselected threshold.

21. A method of identifying possible arc segments for removal in a modulated arc therapy plan, the method comprising:

iteratively optimizing a modulated arc therapy plan for an initial arc segment;

computing a geometric freedom (GF) metric for each control point (CP) of the initial arc segment by operations including:

computing a ratio, for each beamlet of the CP, of a number of tumor voxels touched by a beamlet divided by a sum of a number of voxels of critical organs touched by the beamlet;

summing the GF metric values for the beamlets of the CP to generate the GF metric for the CP;

determining contiguous groups of CPs with GF metric values below a pre-selected threshold as candidate arc segments for removal from the modulated arc therapy plan; and estimating a re-distribution of a dose of the modulated arc therapy plan with the candidate arc segments removed from the modulated arc therapy plan.

22. The method of claim 21, further including:

plotting, on a display device, a graph of the GF metric as a function of each CP along the initial arc segment;

determining GF metric values as a function of CP on the graph being below a preselected threshold;

determining contiguous groups of CPs with GF metric values below the pre-selected threshold as candidate arc segments for removal from the modulated arc therapy plan; and estimating a re-distribution of a dose of the modulated arc therapy plan with the candidate arc segments removed from the modulated arc therapy plan.

23. The method of claim 21, further including:

estimating dose objectives of the modulated arc therapy plan with the GF metrics of each CP and an initial modulated arc therapy plan; and re-estimating the dose objectives when below a preselected threshold by adjusting a size of at least one of the candidate arc segments until the dose objectives are no longer below the preselected threshold.

* * * * *